(12) United States Patent
Murakami

(10) Patent No.: US 9,297,740 B2
(45) Date of Patent: Mar. 29, 2016

(54) PARTICLE DETECTING DEVICE AND PARTICLE DETECTING METHOD

(71) Applicant: Azbil Corporation, Tokyo (JP)

(72) Inventor: Hisaya Murakami, Tokyo (JP)

(73) Assignee: AZBIL CORPORATION, Tokyo (JP)

( * ) Notice: Subject to any disclaimer, the term of this patent is extended or adjusted under 35 U.S.C. 154(b) by 97 days.

(21) Appl. No.: 14/279,651

(22) Filed: May 16, 2014

(65) Prior Publication Data

US 2014/0340681 A1    Nov. 20, 2014

(30) Foreign Application Priority Data

May 17, 2013    (JP) ................... 2013-105318

(51) Int. Cl.
| | |
|---|---|
| *G01N 15/14* | (2006.01) |
| *G01N 21/51* | (2006.01) |
| *G01N 21/64* | (2006.01) |
| *G01N 15/06* | (2006.01) |
| *G01N 21/53* | (2006.01) |
| *G01N 1/22* | (2006.01) |

(52) U.S. Cl.
CPC ............ *G01N 15/1404* (2013.01); *G01N 15/06* (2013.01); *G01N 21/51* (2013.01); *G01N 21/53* (2013.01); *G01N 1/2273* (2013.01); *G01N 21/64* (2013.01); *G01N 2015/0693* (2013.01)

(58) Field of Classification Search
USPC ............... 356/335–343; 250/435, 222.2, 573, 250/458.1
See application file for complete search history.

(56) References Cited

U.S. PATENT DOCUMENTS

| | | | |
|---|---|---|---|
| 3,513,636 A | 5/1970 | Halasz et al. | |
| 3,787,122 A | 1/1974 | Lepper, Jr. | |
| 4,113,386 A * | 9/1978 | Lepper, Jr. | G01N 21/53 250/574 |
| 5,245,405 A * | 9/1993 | Mitchell | G01N 21/15 356/245 |
| 6,211,956 B1 * | 4/2001 | Nicoli | G01N 15/02 356/337 |
| 2002/0134438 A1* | 9/2002 | Vilagines | F16K 37/0058 137/559 |
| 2003/0020910 A1* | 1/2003 | Peterson | G01N 15/1459 356/338 |
| 2007/0281371 A1* | 12/2007 | Miller | B01L 3/502761 436/526 |
| 2011/0050200 A1* | 3/2011 | Tartagni | G01N 15/1056 324/71.4 |

(Continued)

FOREIGN PATENT DOCUMENTS

| | | |
|---|---|---|
| DE | 10 2010 002 424 | 9/2011 |
| FR | 1529083 | 6/1968 |

(Continued)

OTHER PUBLICATIONS

Hasegawa, N et al., "Instantaneous Bioaerosol Detection Technology and Its Application", azbil Technical Review, 2009, pp. 2-7.

(Continued)

*Primary Examiner* — Sang Nguyen
(74) *Attorney, Agent, or Firm* — Troutman Sanders LLP

(57) ABSTRACT

A particle detecting device includes a frame, a chamber that is disposed within the frame, a sample injection flow path for injecting, into the chamber, a fluid that includes particles, from a first inlet opening that is provided in the frame, an adjusting mechanism that adjusts a state of the fluid within the chamber by supplying a fluid, from which the particles have been removed, into the chamber through an adjusting flow path that connects to the chamber from a second inlet opening that is separate from the first inlet opening that is provided in the frame, and a detecting mechanism that detects particles included within the fluid, by shining a light into the fluid within the chamber.

14 Claims, 3 Drawing Sheets

(56) References Cited

U.S. PATENT DOCUMENTS

2011/0317162 A1    12/2011    DeFreez et al.
2013/0047703 A1    2/2013    Stengel et al.
2013/0248693 A1*    9/2013    Buchanan, III ………. G01V 8/10
                                                                                       250/222.2

FOREIGN PATENT DOCUMENTS

GB          WO0063673    * 10/2000   ………. G01N 15/14
JP          2008-225539      9/2008
JP          2011-83214      4/2011

OTHER PUBLICATIONS

European Search Report dated Jan. 8, 2015, which issued during prosecution of European Application No. 14167907.6.

* cited by examiner

PARTICLE DETECTING DEVICE AND PARTICLE DETECTING METHOD

CROSS REFERENCE TO RELATED APPLICATION

This application claims priority under 35 U.S.C. §119 to Japanese Patent Application No. 2013-105318, filed on May 17, 2013, the entire content of which being hereby incorporated herein by reference.

FIELD OF TECHNOLOGY

The present invention relates to an environment evaluating technology, and, in particular, relates to a particle detecting device and particle detecting method.

BACKGROUND ART

In ordinary rooms or in clean rooms, such as bio clean rooms, airborne particles, including microorganisms, are detected and recorded using particle detecting devices. See, for example, Japanese Unexamined Patent Application Publication Nos. 2008-225539 and 2011-83214, and N. Hasegawa, et al., *Instantaneous Bioaerosol Detection Technology and Its Application*, azbil Technical Review, 2-7, Yamatake Corporation, December 2009. An optical particle detecting device draws in air from the room wherein the device is installed, for example, and illuminates the drawn-in air with light. When there is a particle included within the air, a particle that is illuminated with light emits fluorescence or produces scattered light, enabling detection of the numbers, sizes, and the like, of particles included in the air.

Given this, an aspect of the present invention is to provide a particle detecting device and particle detecting method wherein particles can be detected accurately.

SUMMARY

An aspect of the present disclosure provides a particle detecting device including: (a) a frame; (b) a chamber that is disposed within the frame; (c) a sample injection flow path for injecting, into the chamber, a fluid that includes particles, from a first inlet opening that is provided in the frame; (d) an adjusting mechanism for adjusting the state of the fluid within the chamber by supplying a fluid, from which the particles have been removed, into the chamber through an adjusting flow path that connects to the chamber from a second inlet opening that is separate from the first inlet opening that is provided in the frame; and (e) a detecting mechanism for detecting particles included within the fluid, by shining a light into the fluid within the chamber.

Furthermore, an aspect of the present disclosure provides a particle detecting method, including: (a) injecting a fluid that includes particles into a chamber that is disposed within a frame, through a sample injection flow path, from a first inlet opening that is provided within the frame; (b) adjusting the state of the fluid within the chamber by supplying a fluid, from which the particles have been removed, into the chamber through an adjusting flow path that connects to the chamber from a second inlet opening that is separate from the first inlet opening that is provided in the frame; and (c) detecting particles included within the fluid, by shining a light into the fluid within the chamber.

The present invention enables the provision of a particle detecting device and particle detecting method wherein particles can be detected accurately.

DETAILED DESCRIPTION

Examples of the present invention will be described below. In the descriptions of the drawings below, identical or similar components are indicated by identical or similar codes. Note that the diagrams are schematic. Consequently, specific measurements should be evaluated in light of the descriptions below. Furthermore, even within these drawings there may, of course, be portions having differing dimensional relationships and proportions.

EXAMPLE

Figure 1:
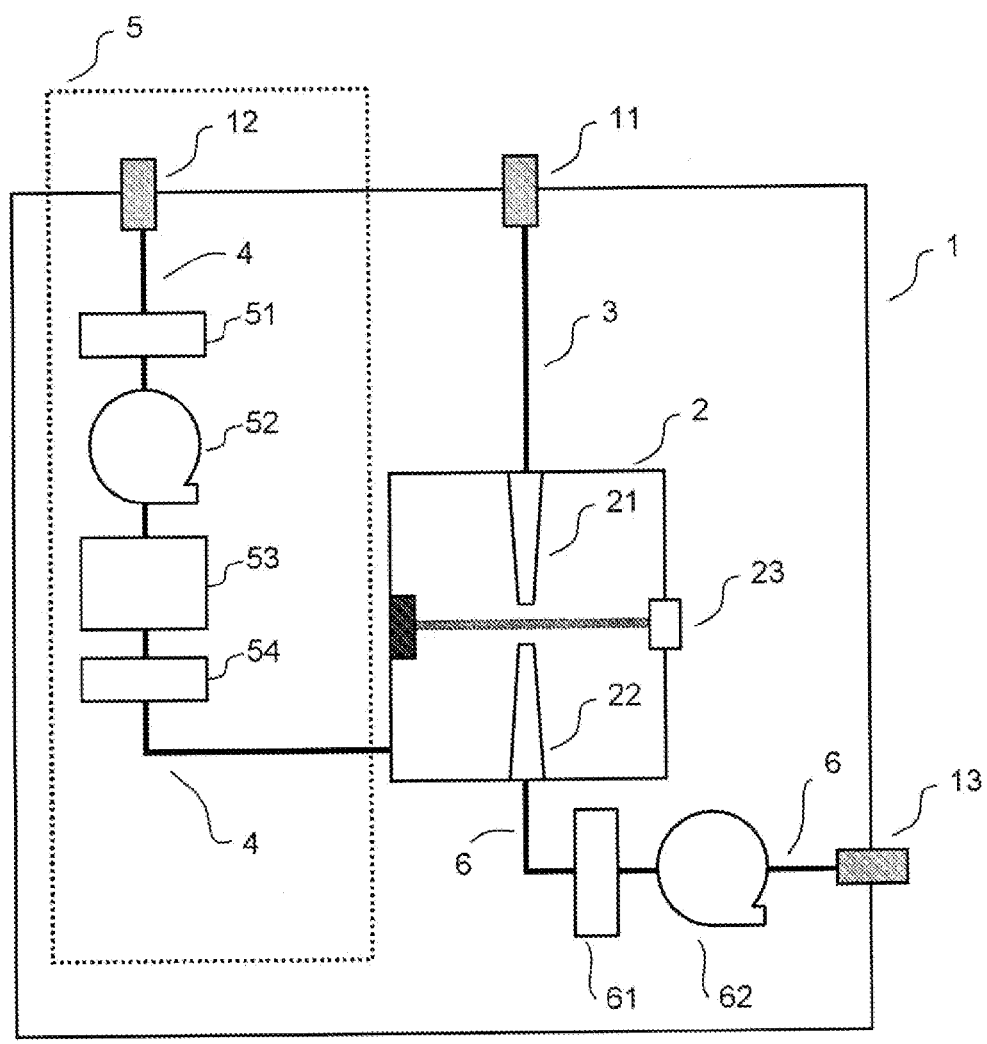
FIG. 1 is a schematic diagram of a particle detecting device as set forth in Example according to the present disclosure.

A particle detecting device as set forth in Example, as illustrated in FIG. 1, including: a frame 1; a chamber 2 that is disposed within the frame 1; an injection nozzle 21 that is disposed within the chamber 2; a sample injection flow path 3 for injecting, into the chamber 2, a fluid that includes particles, connecting between a from a first inlet opening 11 that is provided in the frame 1 and an injection nozzle 21 that is disposed within the chamber 2; an adjusting mechanism 5 for adjusting the state of the fluid within the chamber 2 by supplying a fluid, from which the particles have been removed, into the chamber 2 through an adjusting flow path 4 that connects to the chamber 2 from a second inlet opening 12 that is separate from the first inlet opening 11 that is provided in the frame 1; and a detecting mechanism 23 for detecting particles included within the fluid, by shining a light into the fluid that is blown out from the injection nozzle 21.

The frame 1 is of an arbitrary shape. Metal, plastic, or the like, may be used as the material for the frame 1, but there is no limitation thereto. The shape and material of the chamber 2 are arbitrary. However, preferably the chamber 2 is able to withstand pressure. The sample injection flow path 3 is provided with, for example, a pipe made out of metal, plastic, or the like.

The chamber 2 is provided with a discharge nozzle 22 that opposes the injection nozzle 21. Additionally, an discharge opening 13 is also provided in the frame 1, and a discharge flow path 6, for discharging a fluid from within the chamber 2 to the outside of the frame 1, is provided connecting the discharge nozzle 22 of the chamber 2 and the discharge opening 13 of the frame 1. The discharge flow path 6 is provided with a pipe made from, for example, metal or plastic. A discharge fan pump 62 is provided as a discharge fan in the discharge flow path 6.

The fluid, such as air, or the like, from the outside of the frame 1, that has been drawn in by the discharge fan pump 62 through the first inlet opening 11 of the frame 1, is blown into the chamber 2 through the sample injection flow path 3 and the injection nozzle 21. The fluid that is blown into the chamber 2 is discharged from the chamber 2 through the discharge nozzle 22 that is provided opposing the injection nozzle 21, and then passes through the discharge flow path 6, to be discharged to the outside of the frame 1 from the discharge opening 13 that is provided in the frame 1.

In the detecting mechanism 23, a light is shined on the flow of the fluid, such as air, or the like, that is formed between the injection nozzle 21 and the discharge nozzle 22, to detect the number of particles included within the fluid through, for example, detecting the scattered light produced by the particles. Conversely, the detecting mechanism 23 may detect the number of particles included in the fluid that is introduced into the chamber 2 through the first inlet opening 11 through detecting fluorescence that is produced by particles included within the fluid. Moreover, the detecting mechanism 23 can calculate the density of particles in the fluid through dividing the number of particles detected per unit time by the volume of fluid that is drawn in through the first inlet opening 11 per unit time.

Here "particles" includes biological substances such as microorganisms, chemical substances, and dust such as dirt, grime, etc. Examples of microorganisms include bacteria and fungi. Gram-negative bacteria and Gram-positive bacteria can be listed as examples of bacteria. *Escherichia coli*, for example, can be listed as an example of a Gram-negative bacterium. *Staphylococcus epidermidis, Bacillus atrophaeus, Micrococcus lylae*, and *Corynebacterium afermentans* can be listed as examples of Gram-positive bacteria. *Aspergillus* species such as *Aspergillus niger* can be listed as examples of fungi. However, the microorganisms are not limited to these examples.

When a fluorescent particle, such as a microorganism, is included, the particle, when illuminated with light, will emit fluorescent light. For example, riboflavin, flavin nucleotides (FMN), flavin adenine dinucleotide (FAD), nicotinamide adenine dinucleotide phosphate (NAD(P)H), pyridoxamine, pyridoxal phosphate (pyridoxal-5'-phosphate), pyridoxine, tryptophan, tyrosine, phenylalanine, and the like, that are included in the microorganisms will produce fluorescence.

For example, if the particle detecting device is disposed in a clean room, or the like, it may be undesirable for particles to be included in the flow that is discharged to the outside of the frame 1 through the discharge opening 13 that is provided in the frame 1. In such a case, a discharge filter 61, such as a HEPA filter (a High Efficiency Particulate Air filter), or the like, may be provided in the discharge flow path 6.

In the injection nozzle 21 of the chamber 2, the cross-sectional area of the fluid is constricted, increasing the speed of the flow, and decreasing the pressure. Because of this, opposing flows are produced around the flow of the fluid that is formed between the injection nozzle 21 and the discharge nozzle 22. Furthermore, there are cases wherein the discharge of the fluid from the discharge nozzle 22 does not go smoothly because of the drop in pressure within the chamber 2. When opposing flows are produced within the chamber 2 or when there is a pressure drop within the chamber 2, particles may remain stagnant within the chamber 2. When particles remain stagnant within the chamber 2, then the detecting mechanism 23 may count the same particle multiple times, which may make it difficult to detect accurately the number of particles included in a unit volume of the fluid.

In contrast, the particle detecting device according to the Example is provided with an adjusting mechanism 5 for adjusting the state of the fluid within the chamber 2 by increasing the pressure within the chamber 2, or through rectifying the flow of the fluid in the chamber 2, through providing a fluid, from which particles have been removed, into the chamber 2 through an adjusting flow path 4 that connects to the chamber 2 from a second inlet opening 12 that is separate from the first inlet opening 11 that is provided in the frame 1. This makes it possible to discharge smoothly, from the discharge nozzle 22, the fluid that includes the particles.

The adjusting flow path 4 is provided with a pipe that is made from metal, plastic, or the like. A first filter 51, an adjusting pump 52, a flow meter 53, and a second filter 54, for example, are provided in the adjusting flow path 4. The particles that were included in the fluid on the outside of the frame 1, drawn in from the second inlet opening 12 by the adjusting pump 52, are removed by the first filter 51 and the second filter 54. The flow meter 53 measures the flow of, for example, the volume of the fluid from which particles have been removed, supplied per unit time to the chamber 2 by the adjusting pump 52.

Figure 2:
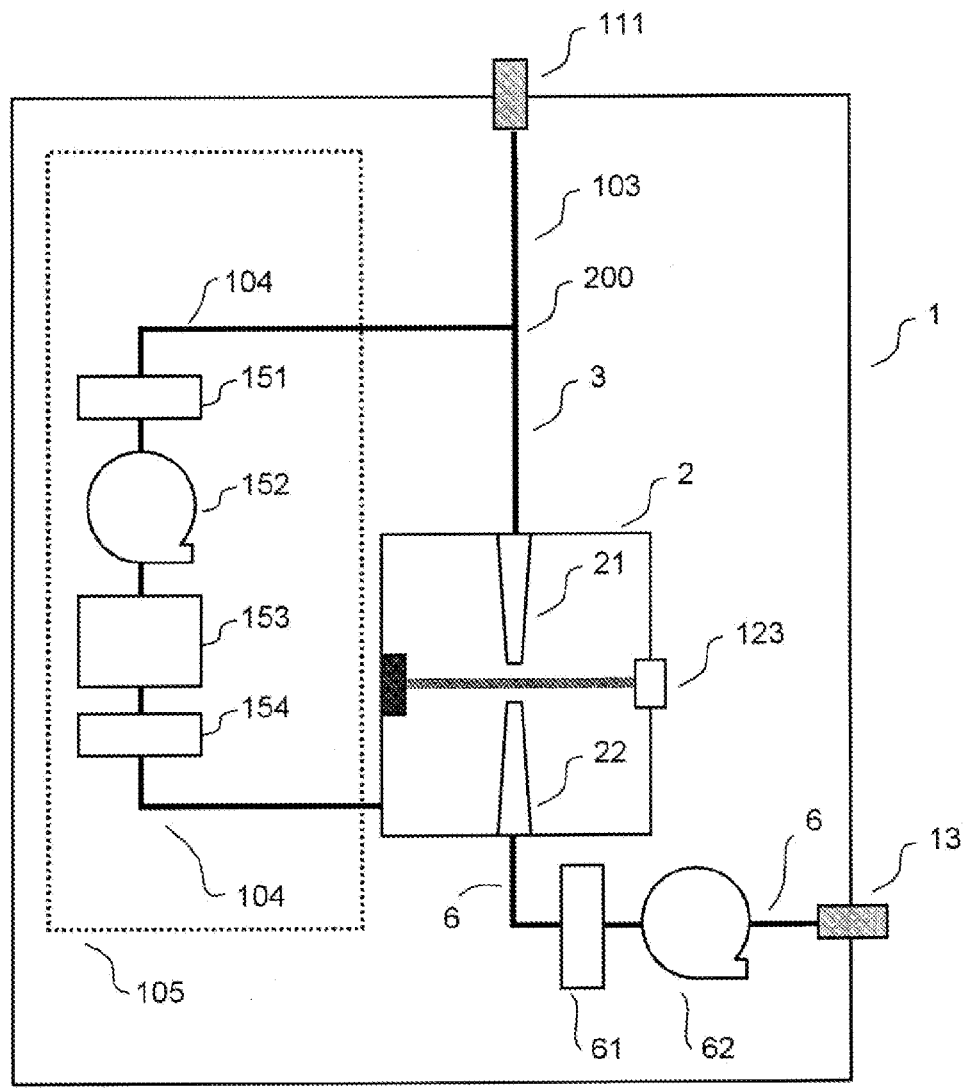
FIG. 2 is a schematic diagram of a particle detecting device according to a comparative example in the present disclosure.

Here, in a reference example of the present disclosure, as illustrated in FIG. 2, a single inlet opening 111 is provided in the frame 1, where the adjusting flow path 104 of the adjusting mechanism 105, and the sample injection flow path 3, are connected to a common flow path 103 that is connected to the single inlet opening 111. The adjusting pump 152 draws a portion of the fluid from the common flow path 103 into the adjusting flow path 104, and the particles that are included in the fluid that has been drawn in are removed by the first filter 151 and the second filter 154. The fluid from which the particles have been removed is provided to the chamber 2 in order to make adjustments such as increasing the pressure within the chamber 2.

The detecting mechanism 123 calculates the density of particles in the fluid by dividing the number of particles detected per unit time by the volume of the fluid that is drawn in into the sample injection flow path 3 per unit time. For example, 40 L of the fluid is drawn in per unit time from a single inlet opening 111, where 10 L of the fluid is distributed to the adjusting flow path 104 at a branching point 200, and 30 L of the fluid is distributed to the sample injection flow path 3. In this case, the detecting mechanism 123 calculates the density of particles by dividing the number of particles detected per unit time by the 30 L that is the volume of the fluid that is distributed to the sample injection flow path 3.

However, the ratio of the number of particles directed toward the adjusting flow path 104 and the number of particles directed toward the sample injection flow path 3 at the branching points 200 is not necessarily equal to the ratio of the volume of the fluid distributed to the adjusting flow path 104 and the volume of the fluid distributed to the sample injection flow path 3. For example, if 10 L of fluid per unit time is distributed to the adjusting flow path 104 and 30 L per unit time of the fluid is distributed to the sample injection flow path 3, then the ratio of the volume of the fluid distributed to the adjusting flow path 104 to the volume of the fluid distributed to the sample injection flow path 3 is 1:3. However, at the branching point 200, if the common flow path 103 and the sample injection flow path 3 are disposed so as to be on a straight line, than the inertia of the particles will tend to cause a larger number of particles to flow into the sample injection flow path 3 than into the adjusting flow path 104. The present inventor discovered that, because of this, when the density of particles in the fluid is calculated by dividing the number of particles detected by the detecting mechanism 123 by the volume of fluid that is distributed to the sample injection flow path 3, the result may be higher than the actual density.

In contrast, in the particle detecting device according to the Example, illustrated in FIG. 1, the adjusting flow path 4 does not branch from the sample injection flow path 3, but rather the fluid that is used for adjusting the pressure within the chamber 2 is drawn in from a second inlet opening 12 that is different from the first inlet opening 11 that is provided in the frame 1. Consequently, the adjusting flow path 4 is independent from the sample injection flow path 3, where the adjusting flow path 4 does not split from the sample injection flow path 3, and thus there will be no error produced even when the density of particles within the fluid is calculated by dividing the number of particles detected per unit time by the detecting mechanism 123 by the volume of the fluid that is drawn in from the first inlet opening 11 per unit time and flows in through the sample injection flow path 3. As a result, the particle detecting device according to the Example enables accurate detection of the number of particles included in the fluid and of the density thereof.

ANOTHER EXAMPLE

Figure 3:
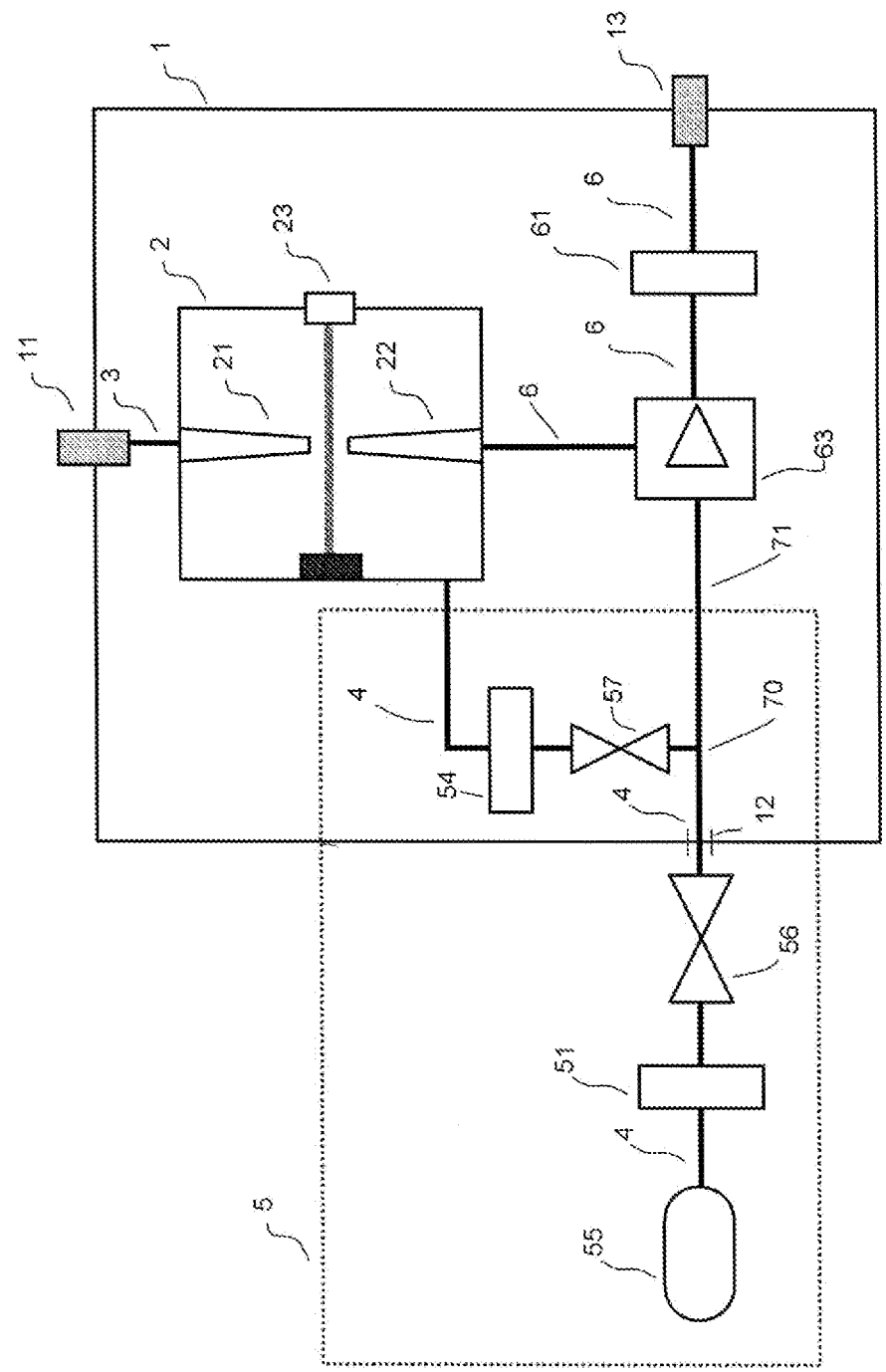
FIG. 3 is a schematic diagram of a particle detecting device as set forth in Another Example according to the present disclosure.

The adjusting mechanism 5 in the particle detecting device according to Another Example is provided with a compressor 55 for compressing air as the fluid, as illustrated in FIG. 3. The compressed air, as the pressurized fluid that is fed from the compressor 55, is sent into the chamber 2 through a first filter 51, a pressure regulator 56, a control valve 57, and a second filter 54. The first filter 51, the pressure regulator 56, the control valve 57, and the second filter 54 are provided in an adjusting flow path 4 that passes through a second inlet opening 12.

A bypass flow path 71 branches from a part 70 between the pressure regulator 56 and the control valve 57 of the adjusting flow path 4, where the bypass flow path 71 joins the discharge flow path 6. The first filter 51 and the second filter 54 remove the particles that are included in the compressed air. The pressure regulator 56 adjusts the pressure of the compressed air that is provided into the chamber 2. The control valve 57 adjusts the allocation ratio between the compressed air that is distributed to the adjusting flow path 4 and the bypass flow path 71.

An ejector 63 is disposed at the confluence portion of the bypass flow path 71 and the discharge flow path 6. The supply of the compressed air from the bypass flow path 71 to the ejector 63 causes the ejector 63 to draw in the fluid from within the chamber 2. The particle detecting device according to the Another Example enables both the supply of compressed air into the chamber 2 and the discharge of air from within the chamber 2 to be performed by the compressor 55, making it possible to simplify the device and reduce the energy consumption.

OTHER EXAMPLES

While there are descriptions of examples as set forth above, the descriptions and drawings that form a portion of the disclosure are not to be understood to limit the present invention. A variety of alternate examples and operating technologies should be obvious to those skilled in the art. For example, the detecting mechanism 23 shown in FIG. 1 and FIG. 3 may measure particles, while airborne, that pass between two laser beams, to calculate the aerodynamic diameters of the particles. In this way, the present invention should be understood to include a variety of examples, and the like, not set forth herein.

The invention claimed is:

1. A particle detecting device comprising:
   a frame;
   a chamber that is disposed within the frame;
   an injection nozzle, disposed within the chamber, connected to a sample injection flow path for injecting, into the chamber, a fluid that includes particles, from a first inlet opening that is provided in the frame;
   a discharge nozzle that is disposed within the chamber, opposing the injection nozzle;
   a discharge flow path, connecting the discharge nozzle to a discharge opening that is provided within the frame, for discharging, to the outside of the frame, the fluid that is within the chamber;
   an adjusting mechanism that adjusts a state of the fluid within the chamber by supplying a fluid, from which the particles have been removed, into the chamber through an adjusting flow path that connects to the chamber from a second inlet opening that is separate from the first inlet opening that is provided in the frame;
   a bypass flow path that branches from the adjusting flow path and joins the discharge flow path, wherein:
      an ejector is disposed at the confluence portion of the bypass flow path and the discharge flow path; and
      a fluid from within the chamber is drawn by the ejector through provision of pressurized fluid from the bypass flow path to the ejector; and
   a detecting mechanism that detects particles included within the fluid, by shining a light into the fluid within the chamber.

2. The particle detecting device as set forth in claim 1, wherein:
   the detecting mechanism detects the number of particles per unit volume of fluid that is injected into the chamber from the first inlet opening.

3. The particle detecting device as set forth in claim 1, wherein:
   the adjusting mechanism comprises:
   an adjusting pump that provides the fluid into the chamber; and a filter that removes the particles that are included in the fluid.

4. The particle detecting device as set forth in claim 1, wherein:
   the adjusting mechanism adjusts the pressure within the chamber.

5. The particle detecting device as set forth in claim 1, wherein:
   the adjusting mechanism rectifies the flow within the chamber.

6. The particle detecting device as set forth in claim 1, wherein:
   the detecting mechanism detects scattered light produced by the particles.

7. The particle detecting device as set forth in claim 1, wherein:
   the detecting mechanism detects fluorescent light produced by the particles.

8. A particle detecting method, comprising:
   injecting a fluid that includes particles into a chamber that is disposed within a frame, through an injection nozzle disposed within the chamber, the injection nozzle being connected to a sample injection flow path, from a first inlet opening that is provided within the frame;
   discharging, to the outside of the frame, fluid from within the chamber, through a discharge flow path connected to a discharge opening that is provided in the frame and a discharge nozzle that is disposed within the chamber facing the injection nozzle;
   adjusting a state of the fluid within the chamber by supplying a fluid, from which the particles have been removed, into the chamber through an adjusting flow path that connects to the chamber from a second inlet opening that is separate from the first inlet opening that is provided in the frame;

providing a pressurized fluid through an ejector to a bypass flow path that branches from the adjusting flow path and joins the discharge flow path, wherein the ejector draws in fluid from within the chamber; and detecting particles included within the fluid, by shining a light into the fluid within the chamber.

9. The particle detecting method as set forth in claim 8, wherein:

in detecting the particles that are included in the fluid, a number of particles per unit volume of fluid that is injected into the chamber from the first inlet opening are detected.

10. The particle detecting method as set forth in claim 8, wherein:

an adjusting pump is used in providing a fluid, from which the particles have been removed, into the chamber through the adjusting flow path; and a filter for removing the particles is provided in the adjusting flow path.

11. The particle detecting method as set forth in claim 8, wherein:

in adjusting the state of the fluid within the chamber, the pressure within the chamber is adjusted.

12. The particle detecting method as set forth in claim 8, wherein:

in adjusting the state of the fluid within the chamber, the flow within the chamber is rectified.

13. The particle detecting method as set forth in claim 8, wherein:

in detecting the particles, scattered light produced by the particles is detected.

14. The particle detecting method as set forth in claim 8, wherein:

in detecting the particles, fluorescent light produced by the particles is detected.

* * * * *